US00PP12953P2

(12) United States Plant Patent
Rother

(10) Patent No.: US PP12,953 P2
(45) Date of Patent: Sep. 10, 2002

(54) CUPHEA PLANT NAMED 'LIGHT LAVENDER II'

(76) Inventor: Reinhard W. Rother, 56 Emerald Monbulk Road, Emerald, Victoria 3782 (AU)

( * ) Notice: Subject to any disclaimer, the term of this patent is extended or adjusted under 35 U.S.C. 154(b) by 32 days.

(21) Appl. No.: 09/834,575

(22) Filed: Apr. 13, 2001

(51) Int. Cl.[7] ..... A01H 5/00

(52) U.S. Cl. ..... Plt./226
(58) Field of Search ..... Plt./226

*Primary Examiner*—Bruce R. Campell
*Assistant Examiner*—Annette Para
(74) *Attorney, Agent, or Firm*—C. A. Whealy

(57) ABSTRACT

A distinct cultivar of Cuphea plant named 'Light Lavender II', characterized by its compact, upright and somewhat outwardly spreading plant habit; freely branching growth habit; glossy dark green leaves; and numerous small light purple-colored flowers.

1 Drawing Sheet

BACKGROUND OF THE INVENTION

The present Invention relates to a new and distinct cultivar of Cuphea plant, botanically known as *Cuphea hyssopifolia*, and hereinafter referred to by the name 'Light Lavender II'.

The new Cuphea is a product of a planned breeding program conducted by the Inventor in Emerald, Victoria, Australia. The objective of the breeding program is to create new Cupheas with numerous flowers with attractive flower colors. The new Cuphea originated from a cross made by the Inventor in 1997 of two unidentified proprietary Cuphea selections. The new Cuphea was selected as a single plant from the resulting progeny by the Inventor in 1997, in Emerald, Victoria, Australia, on the basis of its light purple flower color.

Asexual reproduction of the new cultivar by terminal cuttings taken in Emerald, Victoria, Australia since 1997 has shown that the unique features of this new Cuphea are stable and reproduced true to type in successve generations.

SUMMARY OF THE INVENTION

Plants of the cultivar Light Lavender II have not been observed under all possible environmental conditions. The phenotype may vary somewhat with variations in environment such as temperature, light intensity, daylength, and fertilizer rate without, however, any variance in genotype.

The following traits have been repeatedly observed and are determined to be the unique characteristics of 'Light Lavender II'. These characteristics in combination distinguish 'Light Lavender II' as a new and distinct cultivar:

1. Compact, upright and somewhat outwardly spreading plant habit.

2. Freely branching habit.

3. Glossy dark green leaves.

4. Numerous small light purple-colored flowers.

Plants of the new Cuphea differ from the parent selections and other known Cuphea cultivars primarily in plant habit and flower color as plants of the new Cuphea are more compact and have lighter purple-colored flowers than the parent selections and other known Cuphea cultivars.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Cuphea.

The photograph at the top of the sheet comprises a side perspective view of three typical flowering plants of 'Light Lavender II' grown in a 15-cm container for 8 weeks.

The photograph at the bottom of the sheet comprises a close-up view of typical flowers and leaves of 'Light Lavender II'.

DETAILED BOTANICAL DESCRIPTION

The following observations, measurements and comparisons describe plants grown in Bonsall, Calif., under commercial practice during the summer and autumn in a polyethylene-covered greenhouse with day temperatures ranging from 13 to 35° C. and night temperatures ranging from 13 to 18° C. Three rooted cuttings were planted in 15-cm containers, pinched once and grown for about 8 weeks. In the following description, color references are made to The Royal Horticultural Society Colour Chart except where general terms of ordinary dictionary significance are used.

Botanical classification: *Cuphea hyssopifolia* cultivar Light Lavender II.

Parentage:

*Female parent.*—Unidentified proprietary *Cuphea hyssopifolia* selection, not patented.

*Male parent.*—Unidentified proprietary *Cuphea hyssopifolia* selection, not patented.

Propagation:

*Type cutting.*—Terminal vegetative cuttings.

*Time to initiate roots.*—Summer: About 7 to 12 days at 22 to 24° C. Winter: About 10 to 18 days at 22 to 24° C.

*Time to develop roots, summer and winter.*—About 30 days at 22 to 24° C.

*Root description.*—Fibrous, white.

*Rooting habit.*—Freely branching, dense.

Plant description:

*Form.*—Herbaceous perennial. Compact, upright and somewhat outwardly spreading plant habit. Freely basal branching with about 5 lateral branches per plant; pinching enhances lateral branch development.

*Plant height.*—About 16 cm.

*Plant diameter.*—About 16 cm.

*Vigor.*—Moderately vigorous.

*Lateral branches.*—Length: About 15.5 cm. Diameter: About 2 mm. Internode length: About 1.5 cm. Texture: Pubescent, scattered hairs. Strength: Strong, wiry. Color: 144A overlain with 60C to 60D.

*Foliage description.*—Leaves simple, generally symmetrical and long-persisting; opposite. Quantity per lateral branch: About 36. Length: About 2.5 cm. Width: About 7 mm. Shape: Narrowly elliptic. Apex: Acute. Base: Acute. Margin: Entire. Texture: Smooth, glabrous. Venation pattern: Pinnate. Color: Young foliage, upper surface: 144A, glossy. Young foliage, lower surface: 144B. Mature foliage, upper surface: 147A, glossy; venation, 144C. Mature foliage, lower surface: 147B; venation, 146B. Petiole length: About 2 mm. Petiole diameter: About 1 mm. Petiole color: 144C.

Flower description:

*Flower type and habit.*—Small single salverform flowers; light purple in color; flowers face mostly upward; axillary, typically one flower per axil. Flowers not persistent. Freely flowering, typically about 20 flowers per lateral branch.

*Natural flowering season.*—Flowering continuous and year-round under greenhouse conditions or in subtropical climates.

*Flower longevity on the plant.*—About 7 days in the greenhouse.

*Fragrance.*—None detected.

*Flower size.*—Diameter: About 1 cm. Depth (height): About 1.1 cm. Throat diameter: About 2 mm.

*Flower buds* (*showing color*).—Length: About 6 mm. Diameter: About 2.5 mm. Shape: Elongated oblong, flared at apex. Color: 77A.

*Corolla.*—Arrangement/appearance: Single whorl of six petals, fused at base and separate beyond corolla tube. Petal length from throat: About 5 mm. Petal width: About 3 mm. Petal shape: Roughly spatulate to ovate. Petal apex: Ronded. Petal margin: Entire. Petal texture: Smooth, soft, slightly rugose. Color: Petal, upper surface, when opening: 78B. Petal, lower surface, when opening: 78C. Petal, upper surface and throat, fully opened: 77B. Petal, lower surface and tube, fully opened: 78C.

*Sepals.*—Arrangement/appearance: Single fused tube of six sepals, membranous at apex. Calyx length: About 8 mm. Calyx diameter: About 2 mm. Apex: Shallow acute. Margin: Entire. Texture, both surfaces: Smooth. Color: Upper surface: 145C. Lower surface: 145A to 145B.

*Peduncles.*—Length: About 1 cm. Width: About 1 mm. Angle: About 30° from the stem. Strength: Moderately strong; wiry. Color: 145A.

*Reproductive organs.*—Stamens: Quantity: Six per flower. Anther shape: Elongate, ovate. Anther length: About 1 mm. Anther color: 91B. Pollen amount: Scarce. Pollen color: 4D. Pistils: Quantity: One. Pistil length: About 8 mm. Stigma shape: Elongated, curved, flat. Stigma color: 75A. Style length: About 6 mm. Style color: 155C, Ovary color: 144C.

*Seed.*—Seed production has not been observed.

Disease/pest resistance: Plants of the new Cuphea have not been noted to be resistant to pathogens or pests common to Cuphea.

It is claimed:

1. A new and distinct cultivar of Cuphea plant named 'Light Lavender II', as illustrated and described.

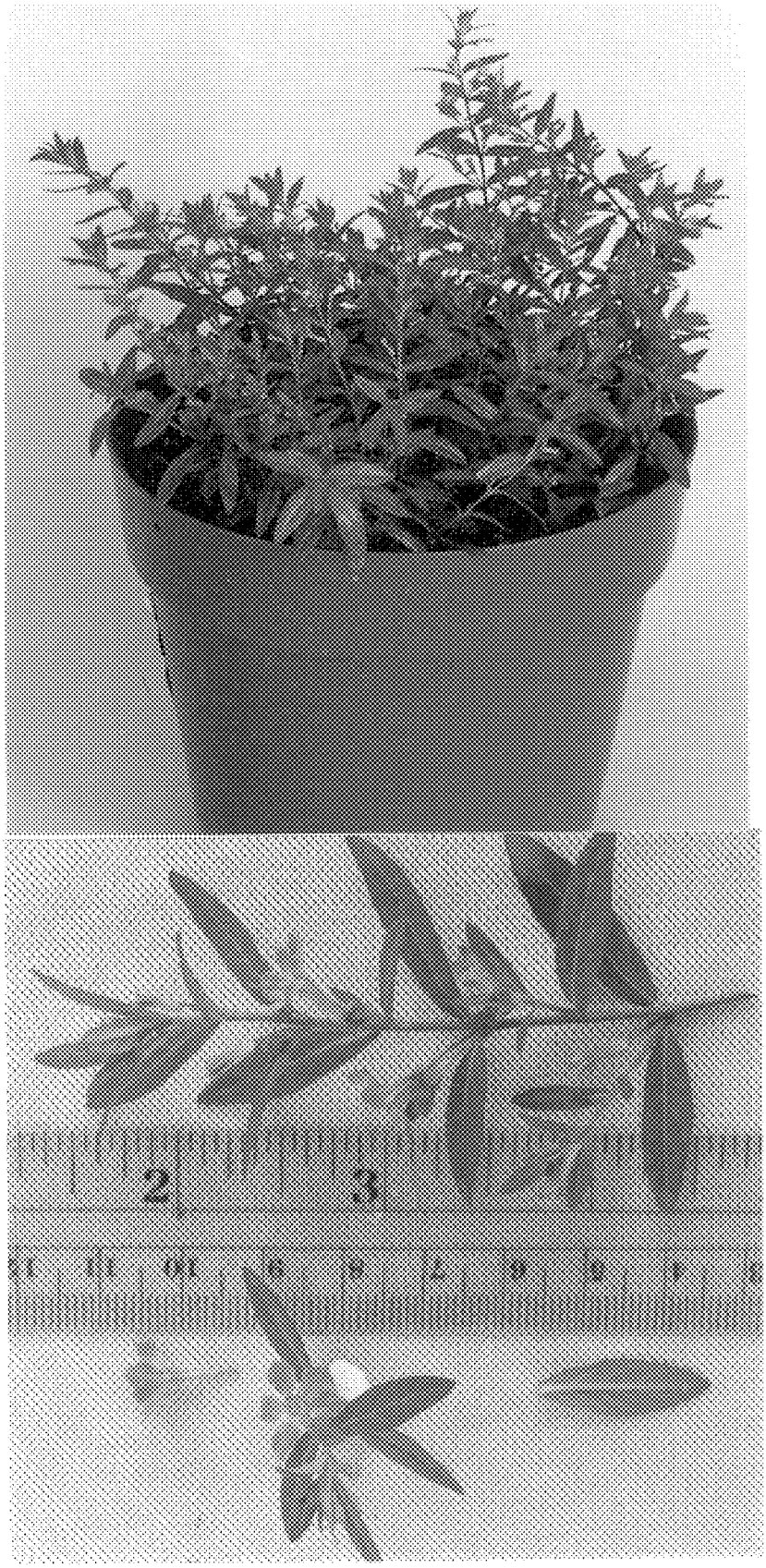

* * * * *